United States Patent [19]

Alaimo

[11] 3,997,538
[45] Dec. 14, 1976

[54] 2-(3,4-DICHLOROPHENYL)-4-(SUB-STITUTED AMINO)-QUINAZOLINES

[75] Inventor: Robert J. Alaimo, Norwich, N.Y.

[73] Assignee: Morton-Norwich Products, Inc., Norwich, N.Y.

[22] Filed: Dec. 29, 1975

[21] Appl. No.: 644,619

[52] U.S. Cl. .................. 260/256.4 B; 260/256.4 Q; 424/251; 260/251 Q
[51] Int. Cl.² ........................................ C07D 239/94
[58] Field of Search ............. 260/256.4 Q, 256.4 B

[56] References Cited
UNITED STATES PATENTS 3,772,295  11/1973  Robba et al. ............... 260/256.4 Q Primary Examiner—Paul M. Coughlan, Jr.
Attorney, Agent, or Firm—Anthony J. Franze

[57] ABSTRACT

A series of 2-(3,4-dichlorophenyl)-4-(substituted amino)quinazolines of the formula:

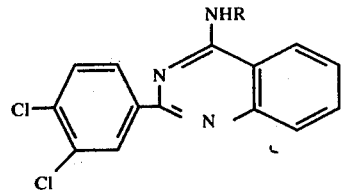

wherein R is (1-pyrrolidinyl)propyl; 3-[bis-(2-hydroxyethyl)amino]propyl; 2,3-dihydroxypropyl; 3-diethylamino-2-hydroxypropyl; or 3-hydroxypropyl and various acid salts are effective antibacterial agents.

6 Claims, No Drawings

2-(3,4-DICHLOROPHENYL)-4-(SUBSTITUTED AMINO)-QUINAZOLINES

This invention is concerned with a series of 2-(3,4-dichlorophenyl)-4-(substituted amino)quinazolines of the formula:

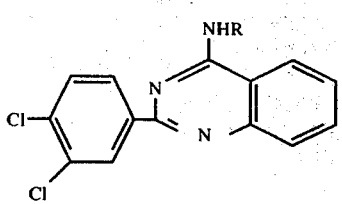

wherein R is (1-pyrrolidinyl)propyl; 3-[bis-(2-hydroxyethyl)amino]propyl; 2,3-dihydroxypropyl; 3-diethylamino-2-hydroxypropyl or 3-hydroxypropyl and various acid salts thereof.

The members of this series of quinazolines are effective antimicrobial agents possessing in vitro antibacterial activity as exemplified in the table herebelow:

| Organism | Minimum inhibitory Concentration in mcg/ml |
| --- | --- |
| S. aureus | 6.25 – 25 |
| S. fecalis | 12.5 – 50 |
| Coryne. liq. | 3.1 – 12.5 |

The results set forth in the table above were secured in the commonly used serial dilution technique for determining in vitro antibacterial effects.

The antibacterial properties of those compounds, make them useful as an active ingredient in various forms such as dusts, sprays, solutions, elixirs, unguents and the like to provide compositions designed to combat bacterial growths.

The methods employed in the preparation of the members of the series of this invention are illustrated in the following examples in order that this invention may be fully available to and understood by those skilled in the art.

EXAMPLE I 2-(3,4-Dichlorophenyl)-4-[3-(1-pyrrolidinyl)propylamino]quinazoline Dihydrochloride To a solution of 4-chloro-2-(3,4-dichlorophenyl)-quinazoline (37.0 g., 0.12 mole) in dimethylformamide (400.0 ml) was added N-(3-aminopropyl) pyrrolidine (31.0 g., 0.24 mole). After stirring and heating the mixture for 4.0 hrs., the mixture was treated with charcoal and filtered. The solution was treated with $H_2O$ and then refrigerated. The cream colored powder removed by filtration was suspended in ethereal hydrochloric acid and treated with ethanol. After cooling, the off-white powder was removed by filtration and weighed 57.0 g., (100%). Two recrystallizations from ethanol + $HCl/CH_3OH$ + HCl/Charcoal (precipitated with ether) provided an analytical sample melting at 261°–263°. Anal. Calcd. for $C_{21}H_{22}Cl_2N_4\cdot 2HCl$: C, 53.18; H, 5.10; N, 11.81. Found: C, 52.96; H, 5.19; N, 11.67.

EXAMPLE II 2-(3,4-Dichlorophenyl)-4-{3-[bis-(2-hydroxyethyl)-amino]propylamino}quinazoline To a solution of 4-chloro-2-(3,4-dichlorophenyl)-quinazoline (31.0 g., 0.1 mole) in dimethylformamide (500.0 ml) was added N-(3-aminopropyl)-diethanolamine (32.0 g., 0.2 mole). The reaction mixture was stirred and heated for 5.0 hr., treated with charcoal, and filtered while still hot. The solution was treated with $H_2O$ until cloudy, then refrigerated. The off-white solid removed by filtration was washed with ethanol and ethyl ether. After air drying, the product weighed 35.0 g., (83%). Recrystallization from $CH_3NO_2$/charcoal provided an analytical sample melting at 102°–106°. Anal. Calcd. for $C_{21}H_{24}Cl_2N_4O_2$: C, 57.93; H, 5.55; N, 12.87. Found: C, 57.58; H, 5.91; N, 12.91.

EXAMPLE III 2-(3,4-Dichlorophenyl)-4-(2,3-dihydroxypropylamino)quinazoline

A mixture of 46.5 g. (0.15 mole) of 4-chloro-2-(3,4-dichlorophenyl)quinazoline in 500 ml of dimethylformamide and 29 g (0.31 mole) of 2,3-dihydroxypropylamine was heated on a steam bath with stirring for 4 hrs. Diluted the mixture with water until turbid and cooled in an ice bath. The colorless solid was filtered and recrystallized from methyl alcohol (Darco). The product was collected as colorless needles melting at 155°–160° (with previous softening) in a yield of 49 g. (90%). Further recrystallization from nitromethane gave 39 g. melting at 162°–164°. Anal. Calcd. for $C_{17}H_{15}Cl_2N_3O_2$: C, 56.06; H, 4.15; N, 11.54 Found: C, 55.63; H, 4.04; N, 11.49.

EXAMPLE IV 2-(3,4-Dichlorophenyl)-4-(3-diethylamino-2-hydroxypropylamino)quinazoline Dihydrochloride Sesquihydrate A mixture of 45 g. (0.145 mole) of 4-chloro-2-(3,4-dichlorophenyl)quinazoline and 44 g. (0.3 mole) of 1-amino-3-diethylamino-2-propanol in 500 ml of dimethylformamide was stirred and heated on a steam bath for 4 hrs. The resulting mixture was diluted with 500 ml of water and was cooled to give 60 g. (95%) of the free base.

This was suspended in ethanol and was saturated with anhydrous hydrogen chloride. The solution was cooled and was diluted with anhydrous ether. An oily material separated and the liquid was removed by decantation. The oily material was recrystallized from isopropanol to give 45 g. (60%) melting at 243°–245°. Recrystallization from isopropanol lowered the melting point to 202°–206°. Anal. Calcd. for $C_{21}H_{24}Cl_2N_4O\cdot 2HCl\cdot 1\text{-}1/2\ H_2O$: C, 48.57; H, 5.63; N, 10.79; Cl, 27.31; Found: C, 48.94; H, 5.34; N, 10.95; Cl, 26.95

EXAMPLE V 2-(3,4-Dichlorophenyl)-4-(3-hydroxypropylamino)-quinazoline

A mixture of 45 g. (0.145 mole) of 4-chloro-2-(3,4-dichlorophenyl)quinazoline and 23 g. (0.31 mole) of 3-hydroxypropylamine in 500 ml of dimethylformamide was heated on a steam bath for 4 hrs. The mixture was diluted with water and cooled and the solid precipitate melting at 164°–166° was collected by filtration in a yield of 50 g. (98%).

Recrystallization from methyl alcohol gave colorless needles melting at 169°–170°. Anal. Calcd. for $C_{17}H_{15}Cl_2N_3O$: C, 58.63; H, 4.34; N, 12.07 Found: C, 58.57; H, 4.34; N, 12.14.

What is claimed is:

1. A compound of the formula:

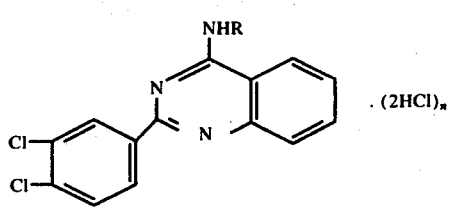

. (2HCl)$_n$ wherein R is (1-pyrrolidinyl)propyl; 3-[bis-(2-hydroxyethyl)amino]propyl; 2,3-dihydroxypropyl; 3-diethylamino-2-hydroxypropyl; or 3-hydroxypropyl and n is 0–1.

2. The compound of claim 1 wherein R is (1-pyrrolidinyl)propyl and n is 1.

3. The compound of claim 1 wherein R is 3-[bis-(2-hydroxyethyl)amino]propyl and n is 0.

4. The compound of claim 1 wherein R is 2,3-dihydroxypropyl and n is 0.

5. The compound of claim 1 wherein R is 3-diethylamino-2-hydroxypropyl and n is 1.

6. The compound of claim 1 wherein R is 3-hydroxypropyl and n is 0.

* * * * *